United States Patent
Li et al.

(10) Patent No.: US 9,994,578 B2
(45) Date of Patent: Jun. 12, 2018

(54) BENZODIAZEPINE DERIVATIVE AND USE THEREOF

(71) Applicant: Qingeng Li, Chongqing (CN)

(72) Inventors: Qingeng Li, Chongqing (CN); Tao Wang, Chongqing (CN); Jianyong Xie, Chongqing (CN); Guisheng Zhang, Chongqing (CN); Xiangqing Xu, Chongqing (CN)

(73) Assignee: JIANGSU NHWALUOKANG PHARMCEUTICAL RESEARCH AND DEVELOPMENT CO., LTD, Xuzhou, Jiangsu (CN)

( * ) Notice: Subject to any disclaimer, the term of this patent is extended or adjusted under 35 U.S.C. 154(b) by 0 days. days.

(21) Appl. No.: 15/327,969

(22) PCT Filed: Jul. 22, 2015

(86) PCT No.: PCT/CN2015/084770
§ 371 (c)(1),
(2) Date: Jan. 20, 2017

(87) PCT Pub. No.: WO2016/011943
PCT Pub. Date: Jan. 28, 2016

(65) Prior Publication Data
US 2017/0217965 A1  Aug. 3, 2017

(30) Foreign Application Priority Data
Jul. 23, 2014  (CN) .......................... 2014 1 0352439

(51) Int. Cl.
*A61K 31/4188* (2006.01)
*A61K 31/5517* (2006.01)
*C07D 487/04* (2006.01)

(52) U.S. Cl.
CPC .................................. *C07D 487/04* (2013.01)

(58) Field of Classification Search
CPC ............ A61K 31/4188; A61K 31/5517; C07D 487/04
See application file for complete search history.

(56) References Cited

FOREIGN PATENT DOCUMENTS

| | | |
|---|---|---|
| CN | 103202815 | 7/2013 |
| CN | 103232454 | 8/2013 |
| CN | 103288834 | 9/2013 |
| CN | 103347519 | 10/2013 |
| WO | WO 2000069836 | 11/2000 |
| WO | WO 2013029431 | 3/2013 |
| WO | WO 2013174883 | 11/2013 |
| WO | WO 2014034890 | 3/2014 |

OTHER PUBLICATIONS

International Search Report of Application No. PCT/CN2015/084770 dated Jan. 28, 2016.

*Primary Examiner* — Brenda L Coleman
(74) *Attorney, Agent, or Firm* — Mark S. Cohen; Pearl Cohen Zedek Latzer Baratz LLP

(57) ABSTRACT

The present invention relates to a new benzodiazepine derivative, pharmaceutically acceptable salt thereof, preparation method therefor, and use thereof. The benzodiazepine derivative and the pharmaceutically acceptable salt thereof of the present invention have obvious anesthetic effect and low toxicity in body, thereby enhancing the medication safety. The benzodiazepine derivative and the pharmaceutically acceptable salt thereof of the present invention have sedative, hypnotic, and anesthetic effect, and can be used as sedative, hypnotic, and anesthetic drugs.

7 Claims, No Drawings

BENZODIAZEPINE DERIVATIVE AND USE THEREOF

CROSS REFERENCE TO RELATED APPLICATION

The present application is a National Phase Application of PCT International Application PCT/CN2015/084770, filed on Jul. 22, 2015, claims priority to and the benefit of Chinese Application No. 201410352439.0, filed on Jul. 23, 2014, all of which are hereby incorporated by reference in their entirety.

TECHNICAL FIELD

Provided are a novel benzodiazepine derivative and a pharmaceutically acceptable salt thereof, a preparation process thereof and use thereof.

BACKGROUND

The benzodiazepine drug is widely clinically used for antianxiety, sedation and hypnosis. As the first water-soluble benzodiazepine derivative, midazolam has been widely used in clinical sedation, hypnosis, analgesia, antiepileptic, antianxiety and general anesthesia. When midazolam is infused as anesthetic into human body, it could be oxidized into α-hydroxyl-midazolam by cytochrome P450 3A4 isoenzyme. The oxidative product still has pharmacological activity, thereby inducing a long time of anesthetic effect and a slow waking up. Accordingly, it is desired for pharmaceutical chemists to develop a novel benzodiazepine water-soluble derivative with faster induction time of anesthesia and shorter maintenance time.

In 1999, remimazolam (CNS7056, formula (III)) has been designed and synthesized by GlaxoSmithKline:

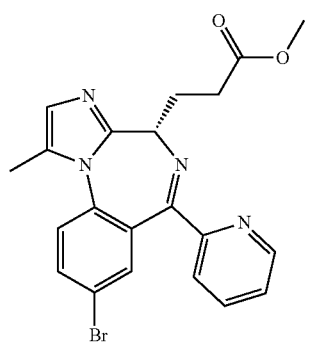

(III)

It attracted great attention in the pharmaceutical industry for the short induction time, low incidence of respiratory depression and short consciousness recovery time. In the sedative clinical trial II of 49 ICU patients in 2013, however, five patients were found to have prolonged waking up time. Five patients have higher serum concentration of remimazolam but the reason was unknown (http://www.paion.de/images/stories/investoren/finanznachrichten/2014/en/japan-telco.pdf). The development was terminated by ONO PHARMACEUTICAL CO., LTD due to unclarity of the metabolism in 2014.

The present inventors designed and synthesized a novel water-soluble benzodiazepine derivative to solve the problem in the prior art, which has lower toxicity after metabolism in vivo and has the advantages of fast action, short maintaining time and rapid recovery.

SUMMARY

In the first aspect, provided is a compound of formula (I) or a pharmaceutically acceptable salt thereof:

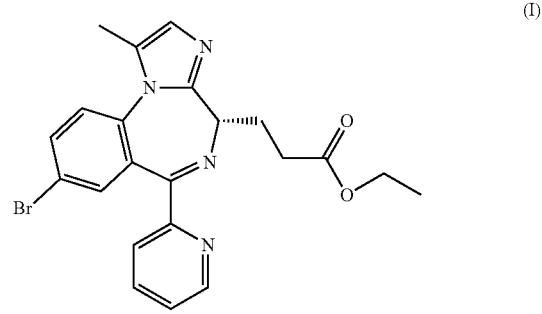 [SMILES: CCOC(=O)CC[C@@H]1N=C(c2ccccn2)c2cc(Br)ccc2-n2c(C)cnc21]

(I)

In an embodiment of the first aspect, provided is a compound of formula(I) or a pharmaceutically acceptable salt thereof, which is characterized in that, methanol and/or formic acid are not generated after metabolism in vivo.

In another embodiment of the first aspect, the pharmaceutically acceptable salt of the compound of formula (I) has formula (Ia):

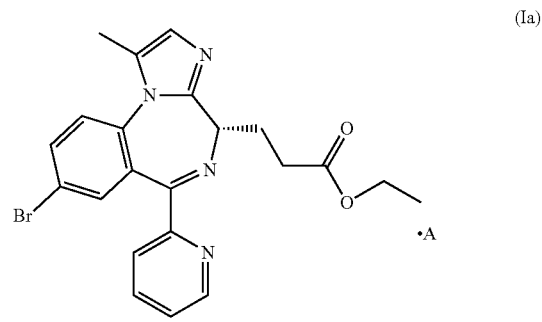

(Ia)

wherein A is an acid that can form a salt with the nitrogen atom containing a lone pair of electrons.

In one specific embodiment, A in formula (Ia) is a pharmaceutically acceptable acid.

The pharmaceutically acceptable salt of the compound of formula (I) may be presented as the formula below:

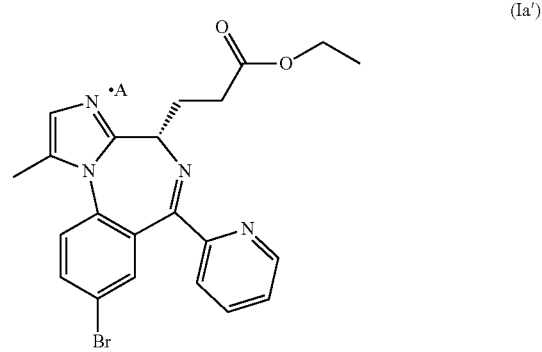

(Ia')

wherein A is as defined above.

Formula (Ia) and formula (Ia') have the same meanings and may be used interchangeably herein.

In a particular embodiment, A is selected from the group consisting of HCl, HBr, acetic acid (AcOH), propionic acid (EtCOOH), sulfuric acid, phosphoric acid, carbonic acid, methanesulfonic acid, ethanesulfonic acid, benzenesulfonic acid, p-toluenesulfonic acid, lactic acid, succinic acid, maleic acid, fumaric acid, tartaric acid, citric acid, malic acid and any combination thereof. In a further preferred embodiment, A is selected from the group consisting of HCl, HBr, methanesulfonic acid, ethanesulfonic acid, benzenesulfonic acid, p-toluenesulfonic acid and any combination thereof.

In another embodiment, provided is a compound of formula (I) or a pharmaceutically acceptable salt thereof for use in providing anesthesia.

In a further embodiment, provided is a compound of formula (I) or a pharmaceutically acceptable salt thereof for use in providing sedation, In the second aspect, provided is a use of a compound of formula (I) or a pharmaceutically acceptable salt thereof for the manufacture of a medicament for providing anesthesia, particularly in preoperative anesthesia, induction of anesthesia and maintenance of anesthesia. In a preferable embodiment, the medicament is administrated intravenously, In an embodiment of the second aspect, provided is a method for providing anesthesia to a subject in need thereof, comprising administrating a compound of formula (I) or a pharmaceutically acceptable salt thereof to the subject. In a preferable embodiment, the compound of formula (I) or the pharmaceutically acceptable salt thereof is administrated intravenously.

In the third aspect, provided is a use of a compound of formula (I) or a pharmaceutically acceptable salt thereof for the manufacture of a medicament for providing sedation. In a preferable embodiment, the medicament is administrated intravenously.

In an embodiment of the third aspect, provided is a method for providing sedation to a subject in need thereof, comprising administrating a compound of formula (I) or a pharmaceutically acceptable salt thereof to the subject. In a preferable embodiment, the compound of formula (I) or the pharmaceutically acceptable salt thereof is administrated intravenously, In the fourth aspect, provided is a pharmaceutical composition, comprising a compound of formula (I) or a pharmaceutically acceptable salt, and a pharmaceutically acceptable carrier.

DETAILED DESCRIPTION

Pharmaceutically Acceptable Salt

According to an embodiment of the invention, the salts according to the invention are those formed between an acid (e.g., inorganic acid or organic acid) and the nitrogen atom containing a lone pair of electrons in compound (I), According to another embodiment of the invention, "a pharmaceutically acceptable salt" of the compound of the invention may be a salt formed with an inorganic acid, such as hydrochloric acid (HCl), hydrobromic acid (HBr), hydroiodic acid, sulfuric acid, pyrosulfuric acid, phosphoric acid or nitric acid; or a salt with an organic acids, such as methanesulfonic acid, ethanesulfonic acid, benzenesulfonic acid, p-toluenesulfonic acid, formic acid, acetic acid, acetoacetic acid, pyruvic acid, trifluoroacetic acid, propionic acid, butyric acid, hexanoic acid, heptanoic acid, undecanoic acid, lauric acid, benzoic acid, salicylic acid, 2-(4-hydroxybenzoyl)benzoic acid, camphoric acid, cinnamic acid, cyclopentanepropionic acid, digluconic acid, 3-hydroxy-2-naphthoic acid, nicotinic acid, pamoic acid, pectinic acid, peroxosulfuric acid, 3-phenylpropionic acid, picric acid, pivalic acid, 2-hydroxyethanesulfonic acid, itaconic acid, sulfamic acid, trifluoromethanesulfonic acid, dodecylsulfuric acid, 2-naphthalenesulfonic acid, naphthalene disulfonic acid, camphorsulfonic acid, citric acid, tartaric acid, stearic acid, lactic acid, oxalic acid, malonic acid, succinic acid, malic acid, adipic acid, alginic acid, maleic acid, fumaric acid, D-gluconic acid, mandelic acid, ascorbic acid, glucoheptonic acid, glycerophosphoric acid, aspartic acid, sulfosalicylic acid, hemisulfuric acid or thiocyanic acid.

According to another embodiment of the invention, the pharmaceutically acceptable salt of the compound of the invention has the formula:

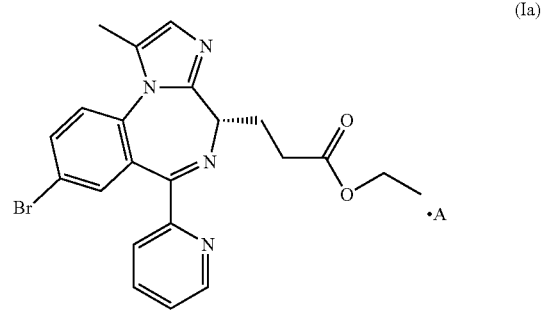

(Ia)

wherein A is selected from the group consisting of one or more of HCl, HBr, acetic acid, propionic acid, sulfuric acid, phosphoric acid, carbonic acid, methanesulfonic acid, ethanesulfonic acid, benzenesulfonic acid, p-toluenesulfonic acid, lactic acid, succinic acid, maleic acid, fumaric acid, tartaric acid, citric acid or malic acid; particularly one or more of HCl, HBr, methanesulfonic acid, ethanesulfonic acid, benzenesulfonic acid, p-toluenesulfonic acid.

In a preferred embodiment of the invention, the compound according to the invention or the pharmaceutically acceptable salt thereof is selected from the group consisting of:
remimazolam acid ethyl ester (compound C1),
remimazolam acid ethyl ester p-toluenesulfonate (compound C2),
remimazolam acid ethyl ester benzene sulfonate (compound C3),
remimazolam acid ethyl ester methanesulfonate (compound C4), and.
remimazolam acid ethyl ester ethanesulfonate (compound C5).

Advantages of the Invention

Without being bound by any theory, it is believed that although remimazolam (CNS 7056, i.e. remimazolam acid methyl ester) has many advantages, it is metabolized in vivo by the carboxylesterase 1 (hCES1) into non-active substance remimazolam acid (CNS 7054, formula(II)) and methanol, Methanol is toxic (Sneyd. JR. New drugs and technologies, intravenous anaesthesia is on the move (again), British Journal of Anaesthesia. 2010,105 (3): 246~54) and could be further metabolized into formic acid, which has greater toxicity (Tephly TR. The toxicity of methanol, [J]. Life Sci, 1991, 48(11): 1031-1041) and is slowly metabolized as well as easy to accumulate in vivo (Roe. Species differences in methanol poisoning,[J].Crit Rev Toxicol, 1982, 10(4): 275-286).

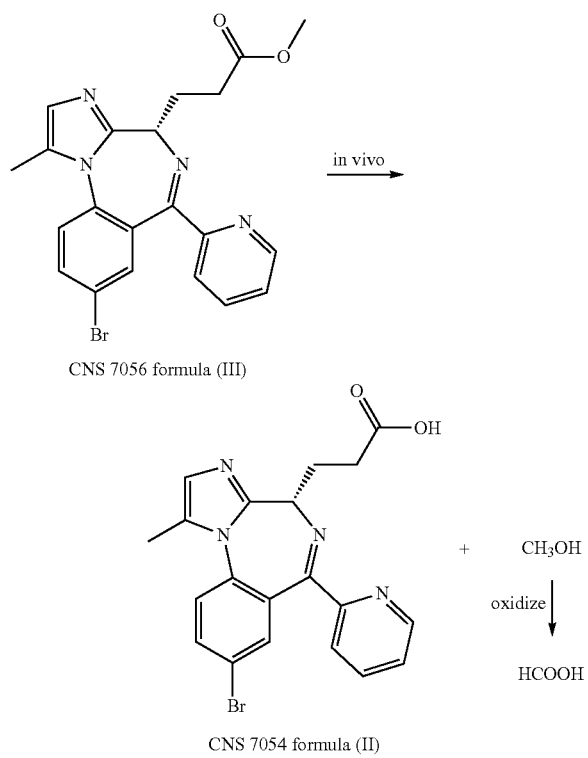

The inventors conducted a hepatocyte metabolism experiment of CNS 7056 in vitro and surprisingly found that when formic acid was added in liver cell nutrient solution in an amount of 0.1% (v/v), the metabolism of CNS 7056 was totally inhibited. Therefore, after a long-term administration of remimazolam during ICU sedation process by ONO PHARMACEUTICAL CO., LTD, the metabolite methanol is easily oxidized to formic acid. Formic acid easily accumulates in vivo and inhibits hCES1 such that remimazolam is metabolized slowly, which may cause high serum concentration in some patients.

By comparison, the benzodiazepine derivative and the pharmaceutically acceptable salt thereof according to the invention have fast action, fast recovery, low incidence of respiratory depression and short consciousness recovery time. Meanwhile, after metabolism in vivo, methanol with great toxicity would not be released and thus formic acid, which may inhibit metabolism of the body, would not be produced, and hCES1 in vivo would not be inhibited. Therefore, higher serum concentration and prolonged waking up time after long-term infusion of the patients will not occur and the patients could revive quickly after ceasing administration.

EXAMPLES

To clearly illustrate the objects and technical solutions of the invention, preferable embodiments are described in details. It should be appreciated that the following examples are merely illustrative of the invention rather than limitations thereto. Some non-substantive improvements and adjustments by a person skilled in the art fall into the scope of the claims. The raw materials and reagents are commercially available products.

Preparation examples

Example 1

Preparation of Remimazolam Acid Ethyl ester (C1)

The compound of formula (II) (remimazolam acid) (4.25g, 10 mmol) was dissolved in absolute ethanol (100 ml) on an ice bath and concentrated sulfuric acid (0.5 g) was added. The ice bath was removed, and the reaction mixture was stirred at room temperature for 12 hours and ethanol was evaporated under reduced pressure. The residue was dissolved in ethyl acetate (100 ml). The organic layer was washed with saturated sodium hydrogencarbonate solution (10 ml×2) and then with saturated brine (30 ml×1). The organic layer was dried by anhydrous sodium sulfate and filtered. The organic solvent was evaporated under reduced pressure to obtain colorless oil of 4.1 g and the yield was 91%.

MASS $[M+H]^+$=454.1

$^1$H-NMR (500 MHz, $CDCl_3$)δ:8.52(s,1H),8.06(s,1H), 7.92 (dd,1H),7.78 (d,2H),7.63 (s,1H),7.57 (s,1H),7.43 (s,1H),4.32 (s,1H),4.08 (s,2H), 2.46 (s,2H), 2.34 (d,5H),1.17 (m, 3H).

Example 2

Preparation of Remimazolam Acid Ethyl ester (C1)

The compound of formula (II) (remimazolam acid) (4.25g, 10 mmol) was dissolved in absolute dichloromethane (20 ml) on an ice bath and oxalyl chloride (3 ml) was slowly added dropwise with a drop of DMF (N,N-dimethylformamide). After addition, the ice bath was removed. The reaction mixture was stirred at room temperature for 12 hours and dichloromethane and oxalyl chloride were evaporated under reduced pressure. The residue was dissolved in dichloromethane (20 ml) and added dropwise into absolute dichloromethane solution (15 ml) comprising DMAP (1.83g, 15 mmol) and ethanol (1ml) on the ice bath, and then the reaction was performed for 4 hours. The organic layer was washed with saturated sodium hydrogencarbonate solution (10 ml×2) and then with saturated. brine (30 ml×1), The organic layer was dried by anhydrous sodium sulfate and filtered. The organic solvent was evaporated under reduced pressure to obtain colorless oil of 4.2 g, and the yield was 92.7%.

Example 3

Preparation of Remimazolam Acid Ethyl ester (C1)

The compound of formula (II) (remimazolam acid) (4.25g, 10 mmol) was dissolved in absolute dichloromethane (50 ml) at room temperature, DCC (dicyclohexylcarbodiimide, 3.1 g, 15 mmol) and DMAP (4-N,N-dimethylaminopyridine, 244 mg, 2 mmol) were added successively into the dichloromethane. After stirring at room temperature for 30 min, dichloromethane solution (5 ml) comprising ethanol (0.92 g, 20 mmol) was added. The reaction mixture was reacted at room temperature for 16 hours and filtered. The filtrate was washed with saturated sodium hydrogencarbonate solution (10 ml×2) and with saturated brine (30 ml×1). Then the filtrate was dried by anhydrous sodium sulfate and filtered. The organic solvent was evaporated under reduced pressure and the residue was separated by column chromatography (ethyl acetate: petroleum ether=1: 1) to obtain colorless oil of 3.8 g, and the yield was 83.8%.

Example 4

Preparation of Remimazolam Acid Ethyl ester p-toluenesulfonate (Compound C2)

Remimazolam acid ethyl ester (1 g, 2.2 mmol) was dissolved in ethyl acetate (15 ml) at room temperature. Ethyl acetate (1 ml) comprising p-toluenesulfonic acid (379 mg, 2.2 mol) was added into the mixture and white solid occurred. The mixture were stirred for 3 hours on an ice bath for precipitation of crystal and then filtered. The filter cake was washed with ice-cold ethyl acetate to obtain 0.9 g of remimazolam acid ethyl ester p-toluenesulfonate.
MASS [M+H]$^+$=454.05.
$^1$H-NMR (500 MHz, CDCl$_3$) : δ 8.54 (d, 1H), 8.09 (d, 1H), 7.96 (dd, 1H), 7.82 (d, 2H), 7.72 (d, 2H), 7.48-7.56 (m, 1H), 7.44 (d, 2H), 7.07 (d, 2H), 4.33 (s, 1H), 4.06 (s, 2H), 2.67 (m, 2H), 2.47 (s, 3H), 2.35 (s, 2H), 2.25 (s, 3H), 1.16(m, 3H).

Example 5

Preparation of Remimazolam Acid Ethyl ester Benzene Sulfonate (Compound C3)

The title compound was prepared according to the procedure of Example 4 using benzenesulfonic acid as the acid.

Example 6

Preparation of Remimazolam Acid Ethyl ester Methanesulfonate (Compound C4)

The title compound was prepared according to the procedure of Example 4 using methanesulfonic acid as the acid, Example 7

Preparation of Remimazolam Acid Ethyl ester Ethanesulfonate (Compound C5)

The title compound was prepared according to the procedure of Example 4 using ethanesulfonic acid as the acid.
The structures of the compounds C1-C5 and their solubilities in normal saline are as follows:

| No. | Name | Structure | Acid A | Solubility in normal saline (mg/ml) |
|---|---|---|---|---|
| C1 | remimazolam acid ethyl ester | 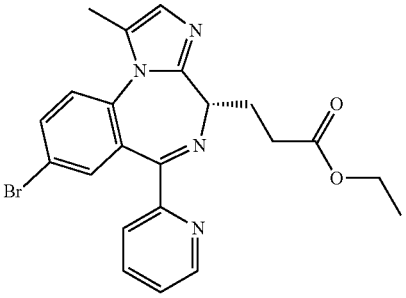 [SMILES: CCOC(=O)CC[C@@H]1N=C(c2ccccn2)c2cc(Br)ccc2-n2c(C)cnc21] | | |
| C2 | remimazolam acid ethyl ester p-toluenesulfonate | 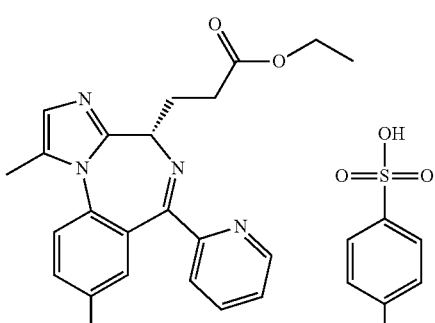 | p-toluenesulfonic acid | 15 |

-continued

| No. | Name | Structure | Acid A | Solubility in normal saline (mg/ml) |
|-----|------|-----------|--------|-------------------------------------|
| C3 | remimazolam acid ethyl ester benzenesulfonate | 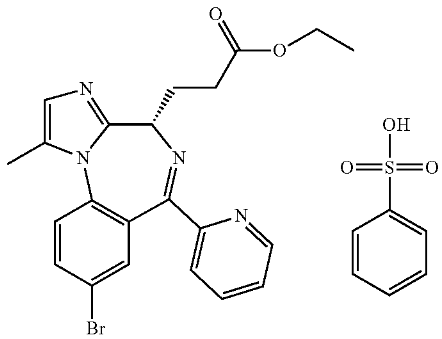 [SMILES: CCOC(=O)CC[C@@H]1N=C(c2ccccn2)c2cc(Br)ccc2-n2c(C)cnc21 ; O=S(=O)(O)c1ccccc1] | benzenesulfonic acid | 15 |
| C4 | remimazolam acid ethyl ester methanesulfonate | 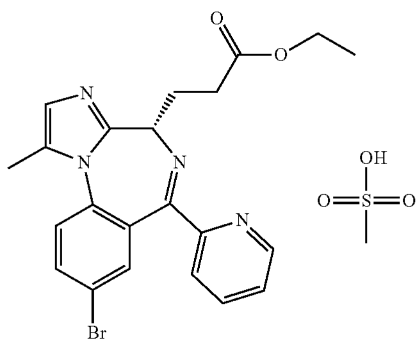 | methanesulfonic acid | 16 |
| C5 | remimazolam acid ethyl ester ethanesulfonate | 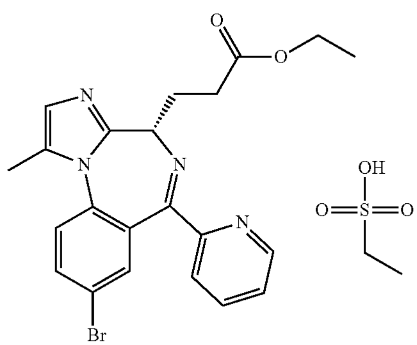 | ethanesulfonic acid | 16 |

Furthermore, other derivatives were also prepared. The structures and solubilities in normal saline are as follows:

| No. | Name | Structure | Acid A | Solubility in normal saline (mg/ml) |
|-----|------|-----------|--------|-------------------------------------|
| C6 | remimazolam acid isopropyl ester p-toluenesulfonate | 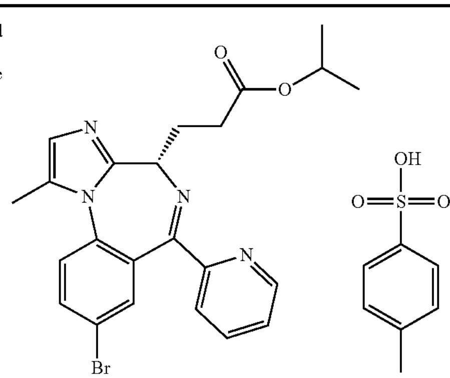 | p-toluenesulfonic acid | 8 |

-continued

| No. | Name | Structure | Acid A | Solubility in normal saline (mg/ml) |
|---|---|---|---|---|
| C7 | remimazolam acid n-propyl ester p-toluenesulfonate | 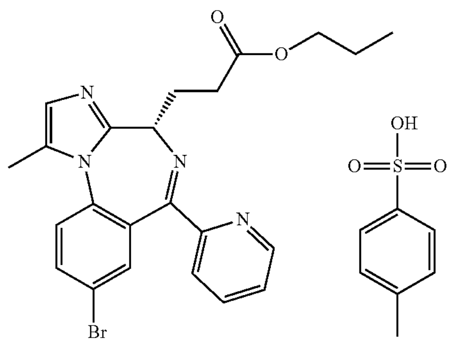 [SMILES: CCCOC(=O)CC[C@@H]1N=C(c2ccccn2)c2cc(Br)ccc2-n2c(C)cnc21 ; Cc1ccc(S(=O)(=O)O)cc1] | p-toluenesulfonic acid | 8 |
| C8 | remimazolam acid isopentyl ester p-toluenesulfonate | 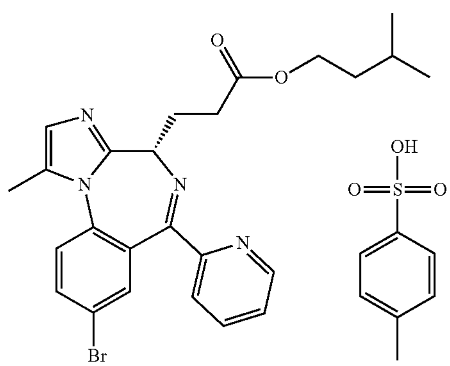 [SMILES: Cc1cnc2n1-c1ccc(Br)cc1C(c1ccccn1)=N[C@H]2CCC(=O)OCCC(C)C ; Cc1ccc(S(=O)(=O)O)cc1] | p-toluenesulfonic acid | 6 |
| C9 | remimazolam acid cyclohexyl ester p-toluenesulfonate | 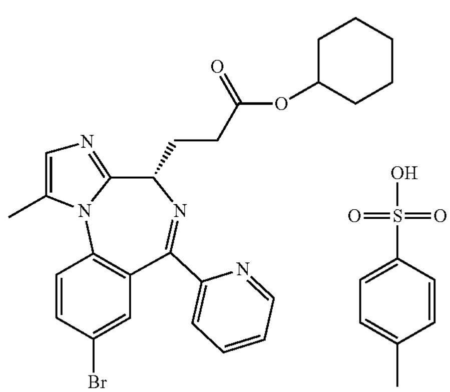 [SMILES: Cc1cnc2n1-c1ccc(Br)cc1C(c1ccccn1)=N[C@H]2CCC(=O)OC1CCCCC1 ; Cc1ccc(S(=O)(=O)O)cc1] | p-toluenesulfonic acid | 5 |

Biological Examples

Example 8

Anesthetic Efficacy of Remimazolam and Compound C2, C6, C7, C8, C9 on Mice

Kunming mice (SPF, Chongqing Medical University Animal Center) were randomly grouped with 6 animals in each group. The dosage as 9 mg/kg was administered via caudal vein injection for 3-5 seconds. The performances during animal experiments were recorded with the standard of disappearance of righting reflex. The experimental results are shown as follows:

| No. | Name of the compound | Administration concentration | Number of anesthetized animals | Behavior of animals |
|---|---|---|---|---|
| Positive control | remimazolam (CNS 7056) | 0.9 mg/ml | 6/6 | Righting reflex disappeared quickly; the mice had steady breath after anesthesia and could quickly walk normally after waking up. |
| C2 | remimazolam acid ethyl ester p-toluenesulfonate | 0.9 mg/ml | 6/6 | Righting reflex disappeared quickly; the mice had steady breath after anesthesia and could quickly walk normally after waking up. |
| C6 | remimazolam acid isopropyl ester p-toluenesulfonate | 0.9 mg/ml | 6/6 | Righting reflex disappeared quickly; the mice had slight breath inhibition after anesthesia. After waking up, the mice showed limbs weakness even paralysis, and could not raise head with eyes closed. Then the mice could crawl slowly without sense of balance, showed hemiplegia, and the body appeared to be swing when walking. |
| C7 | remimazolam acid n-propyl ester p-toluenesulfonate | 0.9 mg/ml | 0/6 | There was no anesthetic effect but some sedative effect. The mice showed limbs weakness and moved slowly. |
| C8 | remimazolam acid isopentyl ester p-toluenesulfonate | 0.9 mg/ml | 0/6 | Non-effect |
| C9 | remimazolam acid cyclohexyl ester p-toluenesulfonate | 0.9 mg/ml | 0/6 | Non-effect |

According to the above results, compound C2 has anesthetic effect on the mice. Although compound C6 has anesthetic effect on the mice, it shows some toxicity. Compounds C7-C9 do not have anesthetic effect on the mice.

Example 9

In vitro Affinity Experiments of Remimazolam, Compound C2 with $GABA_A$ Receptor Benzodiazepines Site The prepared $GABA_A$ (γ-aminobutyric acid) receptor benzodiazepines site membrane (head of living SD rat was cut off on ice and the brain tissue was obtained rapidly and the brain tissue was added into 0.05 M Tris-HCl +1 mM EDTA solution (A) and the solution was homogenized. Then A was added and centrifugation was performed at 1000 r/min for 10 min to obtain the supernatant. The supernatant was centrifuged at 11000 r/min for 30 min at 4° C. Supernatant was discarded, A solution was added and mixture was homogenized with Vortex mixer. Centrifugation was conducted for 3 times. After centrifugation, supernatant was discarded to obtain the sediment.) was dispersed by an appropriate amount of homogenate (50 mM Tris buffer solution, pH 7.4) via homogenizer. 100 μL of the membrane preparation and 100 μL of the homogenate were added into each reaction tube. 100 μL of homogenate was added to total binding tube (TB), and 100 μM of clonazepam (available from Jiangsu Nhwa Pharma) (10 μM final concentration of $1.0 \times 10^{-5}$M) was added to nonspecific binding tube (NB), 100 μL test compound was added to specific binding tube (SB) (final concentration of $10^{-5}$M); 10 L of radioligand$^3$H-flunitrzepam (available from PerkinElmer) was added into each reaction tube (final concentration is 1 nM). Three parallel tubes were set for each reaction tube, and the tubes were placed on ice during sample addition. All the reaction tubes were incubated at 4° C. for 60 min. After reaction, the combined ligands were filtered quickly under reduced pressure (GF/C glass fiber filter paper, available from Whatman). The whatman test paper was immersed in 0.5% PEI and washed with cold experimental buffer solution sufficiently. The filter plate was taken out and put in a 2 ml scintillation vial. 1 ml of toluene scintillation solution (available from Shanghai No. 1 Reagent Factory) was added and mixed uniformly. The scintillation vial was put into liquid scintillation counter (Wallace 1450 MicroBeta Trilux) counting after overnight.

Inhibitory rate (I%)=(total binding tube cpm−compound cpm)/(total binding tube cpm−nonspecific binding tube cpm)×100%.

Inhibitory rate (I %)≥95% means strong affinity with corresponding receptor. The $IC_{50}$ of each compound was calculated by logit method and results are shown as follows:

| Name of the | Inhibitory rate % | | | | | | IC$_{50}$ |
|---|---|---|---|---|---|---|---|
| compound | $1.0 \times 10^{-5}$M | $1.0 \times 10^{-6}$M | $1.0 \times 10^{-7}$M | $1.0 \times 10^{-8}$M | $1.0 \times 10^{-9}$M | $1.0 \times 10^{-10}$M | (nM) |
| remimazolam | 99.7* | 85.5 | 47.0 | 15.4 | 6.8 | 23.0 | 15.8 |
| C2 | 98.0* | 81.9 | 37.7 | 7.9 | 9.5 | 0 | 118 |

*Inhibitory rate ≥95%

According to the above results, the compound C2 has relatively high affinity with GABA$_A$ receptor benzodiazepines site and thus is an effective anesthetic compound like remimazolam.

Example 10

Oil/Water Partition Coefficient of Remimazolam and Compound C2

Remirnazolam and compound C2 were formulated into aqueous solution of 1 mg/ml respectively, 10 ml of prepared solution were measured and n-octanol with equal volume was added. The mixture was stirred at room temperature for 24 hours and the concentrations of each substance in water and oil were measured respectively: logP=−log(C n-octanol/C water), logP of remimazolam is 2.62 and logP of compound C2 is 3.28.

According to the oil/water partition coefficients, compared with remimazolam, compound C2 is more lipophilic and is easier to pass through the blood brain barrier.

Example 11

Rat Plasma Decomposition of Remimazolam and Compound C2

Remimazolam and compound C2 were formulated in normal saline of respectively. 0.1 ml of the solution was measured and added into plasma of rat (living Kunming species, SPF, Animal center of Chongqing Medical University). Mixing was performed sufficiently, and the mixture was placed in constant temperature water bath of 37° C. 2 ml of acetonitrile was added immediately after taking samples at different time-points. Shaking and centrifugation at 1000 rpm/min were conducted to obtain supernatant and HPLC measurement was performed. The results are shown as follows:

| | Name of the | Rat Plasma decomposition in vitro (%) | | |
|---|---|---|---|---|
| No. | compound | 10 s | 30 s | 1 min |
| C2 | remimazolam acid ethyl ester p-toluenesulfonate | 61.4 | 99.0 | 100 |
| Positive control | remimazolam(CNS 7056) | 53.7 | 96.7 | 100 |

According to the above results, the compound C2 has similar metabolic rate as remimazolam.

Example 12

Anesthetic ED$_{50}$ and LD$_{50}$ and TI Index of Rats

Anesthetic ED$_{50}$ (median effective dose) value and LD$_{50}$ (half lethal dose) value of rats are determined by sequential method. Healthy male SD rats (SPF, Qinglongshan animal breeding center of Nanjing), n-10~20, were administrated via caudal vein injection and injection was completed in 10 seconds at a constant speed. The rough dosage that cause anesthesia (or death) of animal was found by preliminary test before experiment and used as middle dosage for the formal experiment. The spacing of each group was set as 0.8, and 2-3 dose-groups were set up and down, respectively. During the formal experiment, administration began from the group of middle dosage. When the animal was anaesthetized (or dead), administration was reduced by a dose unit; if the animal was not anaesthetized (or death), administration was increased by a dose unit until 3-4 reversal were found. The disappearance of righting reflex or death was used as judgment index, respectively. The ot425 software was used to calculate LD$_{50}$ and ED$_{50}$. Treatment index (TI index) was calculated by LD$_{50}$ and ED$_{50}$ value=LD$_{50}$/ED$_{50}$. The experimental results were shown as follows.

| No. | Name of the compound | ED$_{50}$(mg/kg) | LD$_{50}$(mg/kg) | TI index |
|---|---|---|---|---|
| C2 | remimazolam acid ethyl ester p-toluenesulfonate | 3.2(2.64-3.79) | 30.7(28.3-36.2) | 9.6 |
| Positive control | remimazolam (CNS 7056) | 5(3.79-6.59) | 61.4(54.68-71.7) | 12.3 |

According to the above results, the compound or the pharmaceutically acceptable salt thereof according to the invention can cause anesthetic effect on rats like remimazolam,

Example 13

Anesthetic Induction Time and Waking Up Time of Rats Via Intravenous Bolus

Kunming rats (SPF, Qinglongshan animal breeding center of Nanjing), half male and half female, were divided into groups with 10 animals in each group. The dosage of administration was 2*ED$_{50}$ (ED$_{50}$ value was detected in Example 12) and caudal vein injection was done at a constant speed in 10 seconds. The time for the disappearance of right reflex (latent period) and recovery time (duration period) of rats were recorded. The experimental results were shown as follows:

| No. | Name of the compound | Dose (mg/kg) | Number of anesthetic animals | Induction time(s) | Duration (s) |
|---|---|---|---|---|---|
| C2 | remimazolam acid ethyl ester p-toluenesulfonate | 6.4(2*$ED_{50}$) | 10/10 | 18.8 ± 3.0 | 267.4 ± 105 |
| Positive control | remimazolam (CNS 7056) | 10(2*$ED_{50}$) | 10/10 | 52.1 ± 4.7 | 242.2 ± 68 |

According to the above results, the compound or the pharmaceutically acceptable salt thereof according to the invention can provide effective anesthetic effect on rats and the induction time is 2.8 times shorter than that of remimazolam while the waking up time does not have significant difference from that of remimazolam.

It could be found from the above Examples, although compound C2 has a lower affinity to $GABA_A$ receptor benzodiazepines site than remimazolam, the logP of compound C2 is higher than that of remimazolam. Compared with remimazolam, compound C2 can pass through brain blood barrier faster (shorter induction time) and more (lower $ED_{50}$) so as to exert better anesthetic or sedative effect.

Example 14

Rabbits Anesthetic $ED_{50}$

Anesthetic $ED_{50}$ values of rabbits are determined by sequential method. Healthy New Zealand white rabbits (SPF, Peizhou rabbit breeding center) were administrated via ear vein injection at a constant speed in 30 seconds. The rough dosage that cause anesthesia (or death) of animal were found by preliminary test before experiment and used as middle dosage for the formal experiment. The spacing of each group was set as 0.8 and 2-3 dose-groups were set up and down, respectively. The disappearance of righting reflex or death was used as judgment index of efficacy or toxicity, respectively. During the formal experiment, administration began from the group of middle dosage. When the animal was anesthetized (or dead), administration was reduced by a dose unit; if the animal was not anesthetized (or dead), administration was increased by a dose unit, until 3-4 reversal occurred. The disappearance of righting reflex or death was used as judgment index, respectively. The ot425 software was used to calculate $ED_{50}$. The experimental results were shown as follows:

| No. | Name of the compound | $ED_{50}$(mg/kg) |
|---|---|---|
| C2 | remimazolam acid ethyl ester p-toluenesulfonate | 0.512(0.42-0.55) |
| Positive control | remimazolam(CNS 7056) | 0.512(0.44-0.57) |

According to the above results, the compound or the pharmaceutically acceptable salt thereof according to the invention can provide anesthetic effect on rabbits, of which the median effective dosage is comparable with that of remimazolam.

Example 15

Anesthetic Induction Time and Waking Up Time of Rabbits Via Intravenous Bolus

New Zealand white rabbits (SPF, Peizhou rabbit breeding center), half male and half female, were divided into groups with 8 animals in each group. The dosage of administration was 2*$ED_{50}$ ($ED_{50}$ value was detected in Example 14), and was administrated via ear vein injection at a constant speed in 30 seconds. The time (latent period) for the disappearance of right reflex and recovery time (duration period) of rabbits were recorded. The experimental results were shown as follows.

| No. | Name of the compound | Dose (mg/kg) | Number of anesthetic animals | Induction time (min) | Duration (min) |
|---|---|---|---|---|---|
| C2 | remimazolam acid ethyl ester p-toluenesulfonate | 1.0(2*$ED_{50}$) | 8/8 | 1.80 ± 0.78 | 13.19 ± 3.52 |
| Positive control | remimazolam (CNS 7056) | 1.0(2*$ED_{50}$) | 8/8 | 4.30 ± 2.38 | 10.25 ± 2.72 |

According to the above results, the compound or the pharmaceutically acceptable salt thereof according to the invention can provide effective anesthetic effect on rabbits and the induction time is 2.3 times shorter than that of remimazolam while the waking up time does not have significant difference from that of remimazolam.

Example 16

Long-term Venous Infusion Experiment of Compound on Rabbits

New Zealand white rabbits (SPF, Peizhou rabbit breeding center), half male and half female, were divided into groups with 10 animals in each group. The dosage of each administration was 3*$ED_{50}$ ($ED_{50}$ value was detected in Example 14) as inducing dosage when intravenous injection was performed on rabbits. An appropriate dosage was infused as maintaining dosage for 30 min. The infusion rate was adjusted adequately according to the behavior of rabbits during administration to maintain comparable anesthetic depth for each rabbit. The effects of long-term infusion of medicine of the two groups on rabbits (breathe, salivation, excrement) were observed and the time from ceasing administration to the recovery of righting reflex of rabbits were recorded. The experimental results were shown as follows.

| No. | Name of the compound | Inducing dose (mg/kg) | maintaining dose (mg/kg/h) | Waking up time after intravenous drip for 30 min (min) |
|---|---|---|---|---|
| C2 | remimazolam acid ethyl ester p-toluenesulfonate | $1.5(3*ED_{50})$ | 22.5 | $45.20 \pm 12.59$ |
| Positive control | Remimazolam (CNS 7056) | $1.5(3*ED_{50})$ | 22.5 | $33.91 \pm 10.28$ |

According to the above results, the compound or the pharmaceutically acceptable salt thereof according to the invention can provide anesthetic effect on rabbits during continuous intravenous drip, Example 17

Anesthetic Pharmacodynamic Experiment on Macaca Fascicularis

Compound C2 showing significant efficacy on other animal, was administered to Macaca fascicularis for anesthetic pharmacodynamic experiment. The rough anesthetic dosage of compound C2 for Macaca fascicularis was investigated by preliminary test before experiment and different dosages were set for the formal experiment. Intravenous administration was performed in 60±10s. The disappearance of eyelid response of animal was used to judge whether anesthesia occurred on the animal. The behaviors of animals were observed during duration period and the anesthetic effects of compound C2 on Macaca fascicularis were evaluated. The experimental results were shown as follows.

According to the above results, the compound or the pharmaceutically acceptable salt thereof according to the invention can provide significant anesthetic effect on Macaca fascicularis, and the anesthetic effect is stronger than that of remimazolam at 3 mg/kg.

In summary, the compound and the pharmaceutically acceptable salt thereof according to the invention have fast action, fast recovery, low incidence of respiratory depression and short consciousness recovery time and the treating subject could wake up quickly after ceasing administration, showing significant anesthetic effect. The benzodiazepine derivative and the pharmaceutically acceptable salt thereof according to the invention also have fast action and fast waking up upon administration into the subject as intravenous anesthetic. The benzodiazepine derivative and the pharmaceutically acceptable salt thereof according to the invention could also be used to provide sedation in combination with opiates.

Unless otherwise stated, all numbers expressing amount of composition, proportion, condition and the like used in the specification (including the claims) should be understood to be defined by the term "about" under all conditions. Therefore, unless otherwise stated to the contrary, a numerical parameter is approximation and may vary depending

| No. of compound | Dose | Number of anesthetic animal/number of animal | Induction time (s) | Duration (min) | Animal behavior of duration period |
|---|---|---|---|---|---|
| C2 | 3 mg/kg | 3/3 | $2.00 \pm 0.63$ | $28.67 \pm 5.92$ | Limb weakness, loss of consciousness, closed eyelashes, abdominal breathing, steady breathing |
| C2 | 4 mg/kg | 3/3 | $1.74 \pm 0.43$ | $31.67 \pm 6.86$ | Limb weakness, loss of consciousness, closed eyelashes, abdominal breathing, steady breathing |
| C2 | 5 mg/kg | 3/3 | $1.48 \pm 0.54$ | $36.21 \pm 4.78$ | Limb weakness, loss of consciousness, closed eyelashes, abdominal breathing, steady breathing |
| Remimazolam (CNS 7056) | 3 mg/kg | 3/3 | $2.17 \pm 0.41$ | $23.33 \pm 6.71$ | Complete loss of body support, ambiguous consciousness, but consciousness did not completely disappear during the whole process. Head could be raised. |

The invention claimed is:

1. A compound of formula (I) or a pharmaceutically acceptable salt thereof:

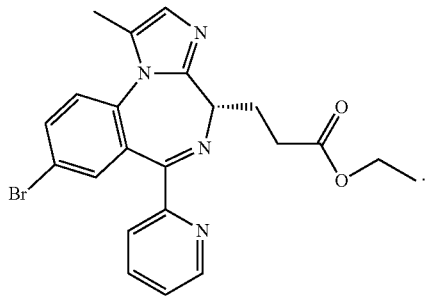
(I)

2. The compound according to claim 1 or the pharmaceutically acceptable salt thereof, wherein the pharmaceutically acceptable salt is presented by formula (Ia):

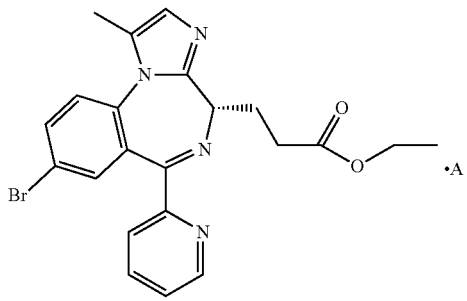
(Ia)

wherein A is an acid that can form a salt with a nitrogen atom containing a lone pair of electrons.

3. The compound according to claim 1 or the pharmaceutically acceptable salt thereof, which is selected from the group consisting of remimazolam acid ethyl ester, remimazolam acid ethyl ester p-toluenesulfonate, remimazolam acid ethyl ester benzenesulfonate, remimazolam acid ethyl ester methanesulfonate and remimazolam acid ethyl ester ethanesulfonate.

4. A pharmaceutical composition, comprising the compound according to claim 1 or the pharmaceutically acceptable salt thereof and a pharmaceutically acceptable carrier.

5. A method for providing anesthesia, comprising administrating the compound according to claim 1 or the pharmaceutically acceptable salt thereof to a subject in need thereof.

6. A method for providing sedation, comprising administrating the compound according to claim 1 or the pharmaceutically acceptable salt thereof optionally in combination with opiates to a subject in need thereof.

7. The compound according to claim 2 or the pharmaceutically acceptable salt thereof, wherein said acid is hydrochloric acid (HCl), hydrobromic acid (HBr), methanesulfonic acid, ethanesulfonic acid, benzenesulfonic acid, p-toluenesulfonic acid, or a combination thereof.

* * * * *